(12) United States Patent
Black et al.

(10) Patent No.: US 9,867,981 B2
(45) Date of Patent: Jan. 16, 2018

(54) INSERTION TOOL FOR IMPLANTING A PADDLE LEAD AND METHODS AND SYSTEMS UTILIZING THE TOOL

(71) Applicant: BOSTON SCIENTIFIC NEUROMODULATION CORPORATION, Valencia, CA (US)

(72) Inventors: James Robert Black, Malibu, CA (US); Anne Margaret Pianca, Santa Monica, CA (US); Joshua Dale Howard, Chatsworth, CA (US); Carolyn Madeleine Noheji, Los Angeles, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 366 days.

(21) Appl. No.: 14/552,328

(22) Filed: Nov. 24, 2014

(65) Prior Publication Data

US 2015/0151114 A1    Jun. 4, 2015

Related U.S. Application Data

(60) Provisional application No. 61/911,737, filed on Dec. 4, 2013.

(51) Int. Cl.
*A61N 1/05* (2006.01)
*A61B 17/34* (2006.01)
*A61B 17/00* (2006.01)

(52) U.S. Cl.
CPC ........ *A61N 1/0553* (2013.01); *A61B 17/3468* (2013.01); *A61B 2017/00738* (2013.01); *A61B 2017/00867* (2013.01)

(58) Field of Classification Search
CPC ........ A61N 1/05; A61N 1/0553; A61N 1/056; A61N 1/0587; A61B 17/3468; A61B 2017/00738; A61B 2017/00867
USPC ........................................... 606/129
See application file for complete search history.

(56) References Cited

U.S. PATENT DOCUMENTS

| 3,646,940 | A | 3/1972 | Timm et al. |
| 3,724,467 | A | 4/1973 | Avery et al. |
| 4,141,365 | A | 2/1979 | Fischell et al. |
| 4,166,469 | A | 9/1979 | Littleford |

(Continued)

FOREIGN PATENT DOCUMENTS

| EP | 1048270 A1 | 11/2000 |
| WO | 2014/099412 | 6/2014 |

*Primary Examiner* — Christopher L Templeton
*Assistant Examiner* — George J Ulsh
(74) *Attorney, Agent, or Firm* — Lowe Graham Jones PLLC; Bruce E. Black

(57) ABSTRACT

An insertion tool for a paddle lead includes an insertion tool body having a receiving end portion; a stylet channel extending along the insertion tool body; a stylet disposed in the stylet channel; and an actuator assembly disposed along the handling end portion of the insertion tool body and coupled to the stylet. The actuator assembly controls transitioning of the stylet between a first position and a second position. In some instances, the stylet can be a wire stylet that is inserted into a lumen in the paddle body of the paddle lead. In some instances, the stylet of the insertion tool pushes lead bodies of the paddle lead out of the insertion tool to release the paddle lead. In some instances, the insertion tool includes a paddle envelope to hold the paddle lead.

20 Claims, 13 Drawing Sheets

(56) References Cited

U.S. PATENT DOCUMENTS

| | | |
|---|---|---|
| 4,270,549 A | 6/1981 | Heilman |
| 4,291,707 A | 9/1981 | Heilman et al. |
| 4,379,462 A | 4/1983 | Borkan et al. |
| 4,512,351 A | 4/1985 | Pohndorf |
| 4,765,341 A | 8/1988 | Mower et al. |
| 4,989,617 A | 2/1991 | Memberg et al. |
| 5,143,067 A | 9/1992 | Rise et al. |
| 5,249,574 A | 10/1993 | Bush et al. |
| 5,282,468 A | 2/1994 | Klepinski |
| 5,391,200 A | 2/1995 | Kenknight et al. |
| 5,397,342 A | 3/1995 | Heil, Jr. et al. |
| 5,417,719 A | 5/1995 | Hull et al. |
| 5,618,287 A | 4/1997 | Fogarty et al. |
| 5,643,330 A | 7/1997 | Holsheimer et al. |
| 5,733,322 A | 3/1998 | Starkebaum |
| 6,027,456 A | 2/2000 | Feler et al. |
| 6,181,969 B1 | 1/2001 | Gord |
| 6,205,361 B1 | 3/2001 | Kuzma et al. |
| 6,249,707 B1 | 6/2001 | Kohnen et al. |
| 6,309,401 B1 | 10/2001 | Redko et al. |
| 6,319,241 B1 | 11/2001 | King et al. |
| 6,415,187 B1 | 7/2002 | Kuzma et al. |
| 6,516,227 B1 | 2/2003 | Meadows et al. |
| 6,522,932 B1 | 2/2003 | Kuzma et al. |
| 6,605,094 B1 | 8/2003 | Mann et al. |
| 6,609,029 B1 | 8/2003 | Mann et al. |
| 6,609,032 B1 | 8/2003 | Woods et al. |
| 6,714,822 B2 | 3/2004 | King et al. |
| 6,741,892 B1 | 5/2004 | Meadows et al. |
| 6,895,283 B2 | 5/2005 | Erickson et al. |
| 7,244,150 B1 | 7/2007 | Brase et al. |
| 7,672,734 B2 | 3/2010 | Anderson |
| 7,761,165 B1 | 7/2010 | He et al. |
| 7,949,395 B2 | 5/2011 | Kuzma |
| 8,224,459 B1 | 7/2012 | Pianca et al. |
| 8,805,543 B2 | 8/2014 | Pianca et al. |
| 8,805,544 B2 | 8/2014 | Pianca et al. |
| 2004/0059392 A1 | 3/2004 | Parramon et al. |
| 2005/0165465 A1 | 7/2005 | Pianca et al. |
| 2007/0150036 A1 | 6/2007 | Anderson |
| 2007/0219595 A1 | 9/2007 | He |
| 2007/0239243 A1 | 10/2007 | Moffitt et al. |
| 2008/0071320 A1 | 3/2008 | Brase |
| 2010/0179562 A1 | 7/2010 | Linker et al. |
| 2011/0319909 A1* | 12/2011 | Thenuwara ........ A61B 17/3468 606/129 |
| 2012/0271315 A1 | 10/2012 | Pianca et al. |
| 2012/0271316 A1 | 10/2012 | Pianca et al. |
| 2012/0283744 A1 | 11/2012 | Stavin |
| 2013/0066331 A1 | 3/2013 | Chitre et al. |
| 2013/0268041 A1 | 10/2013 | Schulte et al. |
| 2013/0289685 A1 | 10/2013 | Browne et al. |
| 2014/0171961 A1 | 6/2014 | Lacey et al. |
| 2015/0151114 A1 | 6/2015 | Black et al. |
| 2015/0258331 A1 | 9/2015 | Dadd et al. |
| 2016/0166828 A1 | 6/2016 | Yu |

* cited by examiner

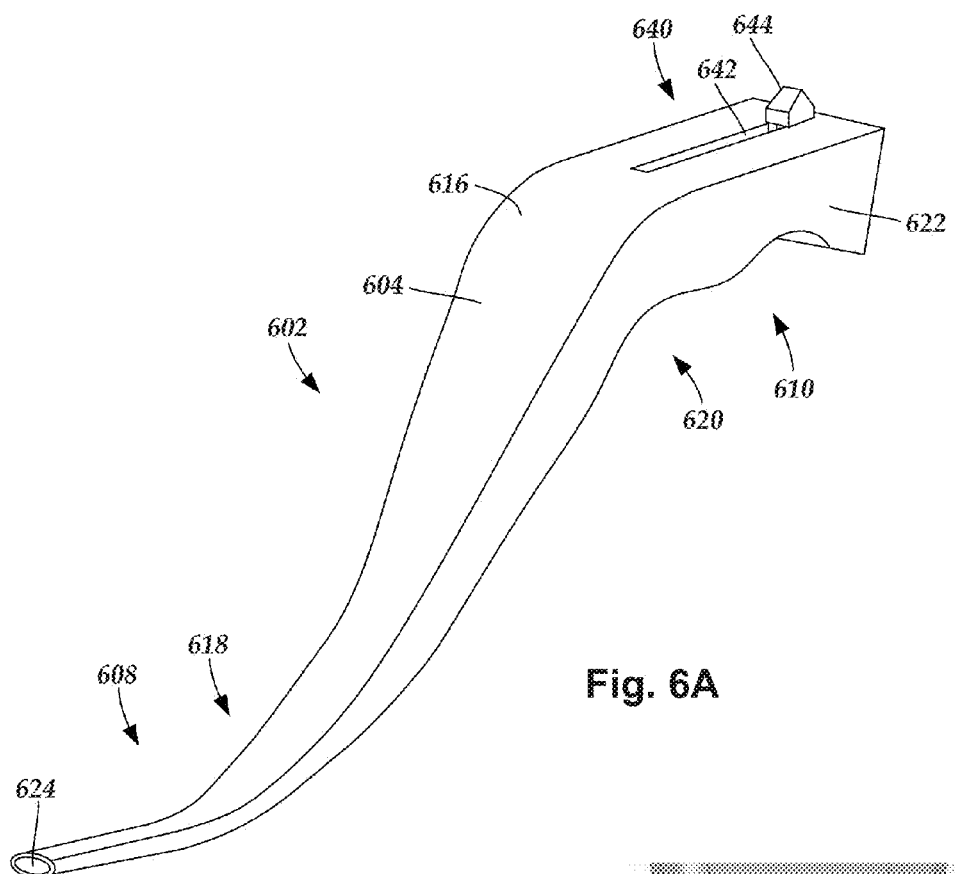
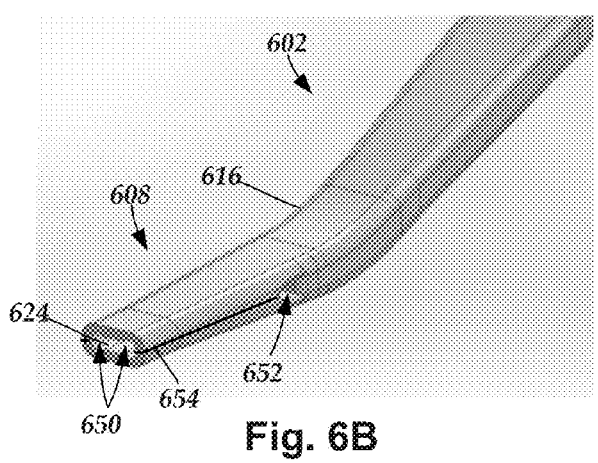
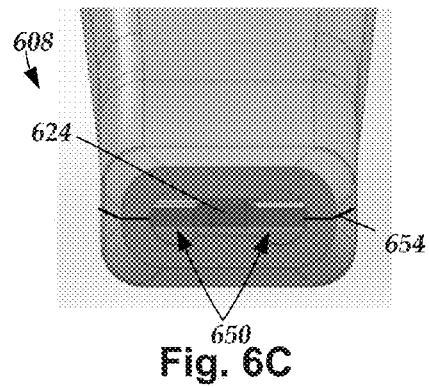
Fig. 6A
Fig. 6B
Fig. 6C

INSERTION TOOL FOR IMPLANTING A PADDLE LEAD AND METHODS AND SYSTEMS UTILIZING THE TOOL

CROSS-REFERENCE TO RELATED APPLICATIONS

This application claims the benefit under 35 U.S.C. §119 (e) of U.S. Provisional Patent Application Ser. No. 61/911,737, filed Dec. 4, 2013, which is incorporated herein by reference.

FIELD

The present invention is directed to the area of implantable electrical stimulation systems and methods of making and using the systems. The present invention is also directed to an insertion tool suitable for facilitating implantation of paddle bodies of electrical stimulation leads, as well as methods of making and using the insertion tool, paddle bodies, leads, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a paddle lead insertion tool including an insertion tool body having a receiving end portion, a handling end portion, an outer surface, and a longitudinal length; a stylet channel extending along the longitudinal length of the insertion tool body from the receiving end portion to the handling end portion; a stylet wire at least partially disposed in the stylet channel, the stylet wire having a first end, a second end, and a curved portion between the first and second ends, the stylet wire forming a partial loop; and an actuator assembly disposed along the handling end portion of the insertion tool body and coupled to the stylet. The actuator assembly includes a first actuator handle attached to the first end of the stylet wire and a second actuator handle attached to the second end of the stylet wire. The insertion tool is configured and arranged to transition the stylet wire between a retracted position and an extended position using the actuator assembly. When the stylet wire is in the retracted position the curved portion of the stylet wire is disposed completely within the stylet channel and when the stylet is in the extended position the curved portion of the stylet extends outwardly from the insertion tool body and is configured and arranged for insertion into a stylet lumen of a paddle lead. The first and second actuator handles, in combination with the wire stylet, are configured and arranged to facilitate steering of a paddle lead to the right or left relative to the receiving end portion of the insertion tool body.

Another embodiment is an insertion tool for a paddle lead. The paddle lead includes a paddle body and at least one lead body extending from the paddle body. The insertion tool includes an insertion tool body having a receiving end portion, a handling end portion, an outer surface, and a longitudinal length. The receiving end portion includes a distal end, at least one lead body channel, at least one exit opening terminating the at least one lead body channel, and at least one slit extending from the distal end to a one of the at least one exit opening. Each of the at least one channel is associated with one of the at least one exit opening and one of the at least one slit with the slit extending from the outer surface of the insertion tool body to the lead body channel. Each of the at least one lead body channel is configured and arranged to receive a one of the at least one lead body extending from the paddle body of the paddle lead. The insertion tool also includes a stylet channel extending along the longitudinal length of the insertion tool body from the receiving end portion to the handling end portion and open to the at least one lead body channel; and a stylet disposed in the stylet channel and having a stylet head disposed in the receiving end portion of the insertion tool body. The stylet is configured and arranged for transitioning between a first position and a second position. When the stylet transitions from the first to the second position, the stylet head pushes any lead body in the at least one lead body channel of the insertion tool body out of the insertion tool through the at least one slit to release the lead body from the insertion tool. The insertion tool further includes an actuator assembly disposed along the handling end portion of the insertion tool body and coupled to the stylet. The actuator assembly is configured and arranged to control transitioning of the stylet between the first position and the second position.

Yet another embodiment is an insertion tool for a paddle lead having a paddle body. The insertion tool includes an insertion tool body having a receiving end portion, a handling end portion, an outer surface, and a longitudinal length; a paddle envelope extending from the receiving end portion and configured and arranged to receive the paddle body of the paddle lead, to hold the paddle body during implantation, and to release the paddle body when directed by a user; a stylet channel extending along the longitudinal length of the insertion tool body from the receiving end portion to the handling end portion; a stylet disposed in the stylet channel and configured and arranged to operate the paddle envelope to hold or release the paddle body; and an actuator assembly disposed along the handling end portion of the insertion tool body and coupled to the stylet. The actuator assembly is configured and arranged to control transitioning of the stylet between a first position and a second position.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 6A is a schematic perspective view of another embodiment of an insertion tool for guiding a paddle lead to a target implantation site within a patient, according to the invention;

FIG. 6B is a schematic perspective view of the receiving end portion of the insertion tool of FIG. 6A, according to the invention;

FIG. 6C is a schematic end view of the receiving end portion of the insertion tool of FIG. 6A, according to the invention;

DETAILED DESCRIPTION

The present invention is directed to the area of implantable electrical stimulation systems and methods of making and using the systems. The present invention is also directed to an insertion tool suitable for facilitating implantation of paddle bodies of electrical stimulation leads, as well as methods of making and using the insertion tool, paddle bodies, leads, and electrical stimulation systems.

Suitable implantable electrical stimulation systems include, but are not limited to, at least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; and 7,761,165; and U.S. Patent Applications Publication Nos. 2005/0165465, 2007/0150036; 2007/0219595; 2007/0239243; and 2008/0071320, all of which are incorporated by reference.

Figure 1:
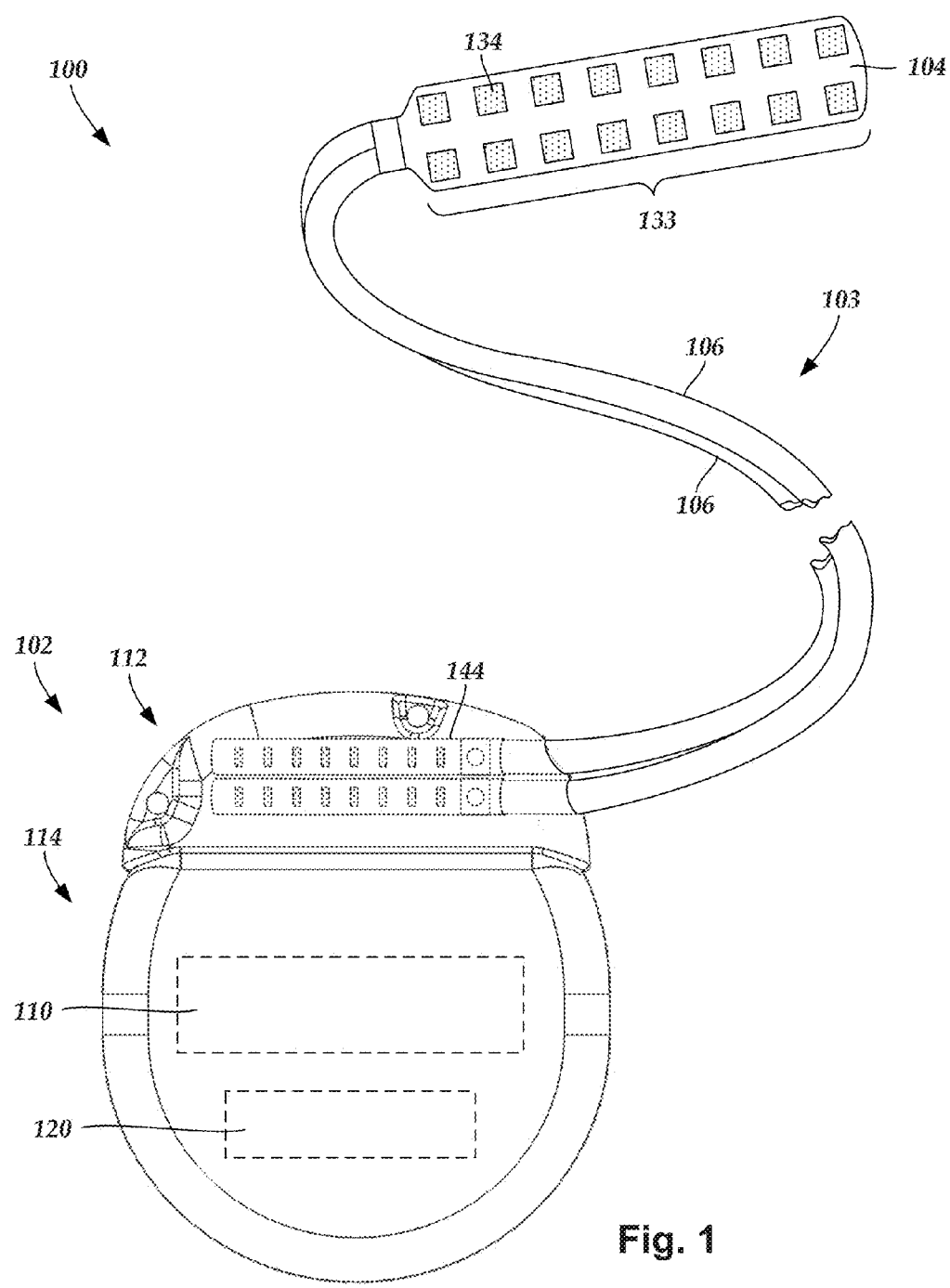
FIG. 1 is a schematic side view of one embodiment of an electrical stimulation system that includes a lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 210 in FIG. 2A-2B) is disposed along each of the one or more lead bodies 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices. For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the paddle body including, for example, four, five, six, seven, eight, nine, ten, eleven, twelve, fourteen, sixteen, twenty-four, thirty-two, or more electrodes 134. The electrodes 134 can be disposed on the paddle body 104 in any suitable arrangement. In FIG. 1, the electrodes 134 are arranged into two columns, where each column has eight electrodes 134.

The electrodes of the paddle body 104 are typically disposed in, or separated by, a non-conductive, biocompatible material such as, for example, silicone, polyurethane, polyetheretherketone ("PEEK"), epoxy, and the like or combinations thereof. The paddle body 104 and the one or more lead bodies 106 may be formed in the desired shape by any process including, for example, molding (including injection molding), casting, and the like. The non-conductive material typically extends from the paddle body 104 to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Figure 2A:
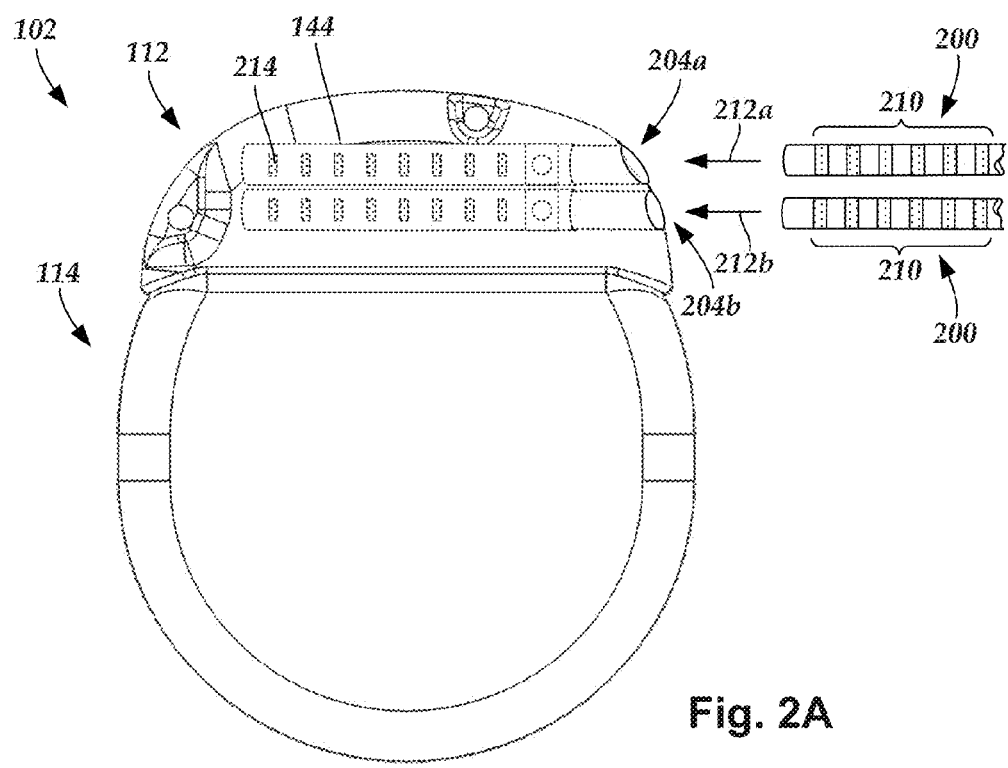
FIG. 2A is a schematic side view of one embodiment of the control module of FIG. 1 configured and arranged to electrically couple to an elongated device, according to the invention.
Figure 2B:
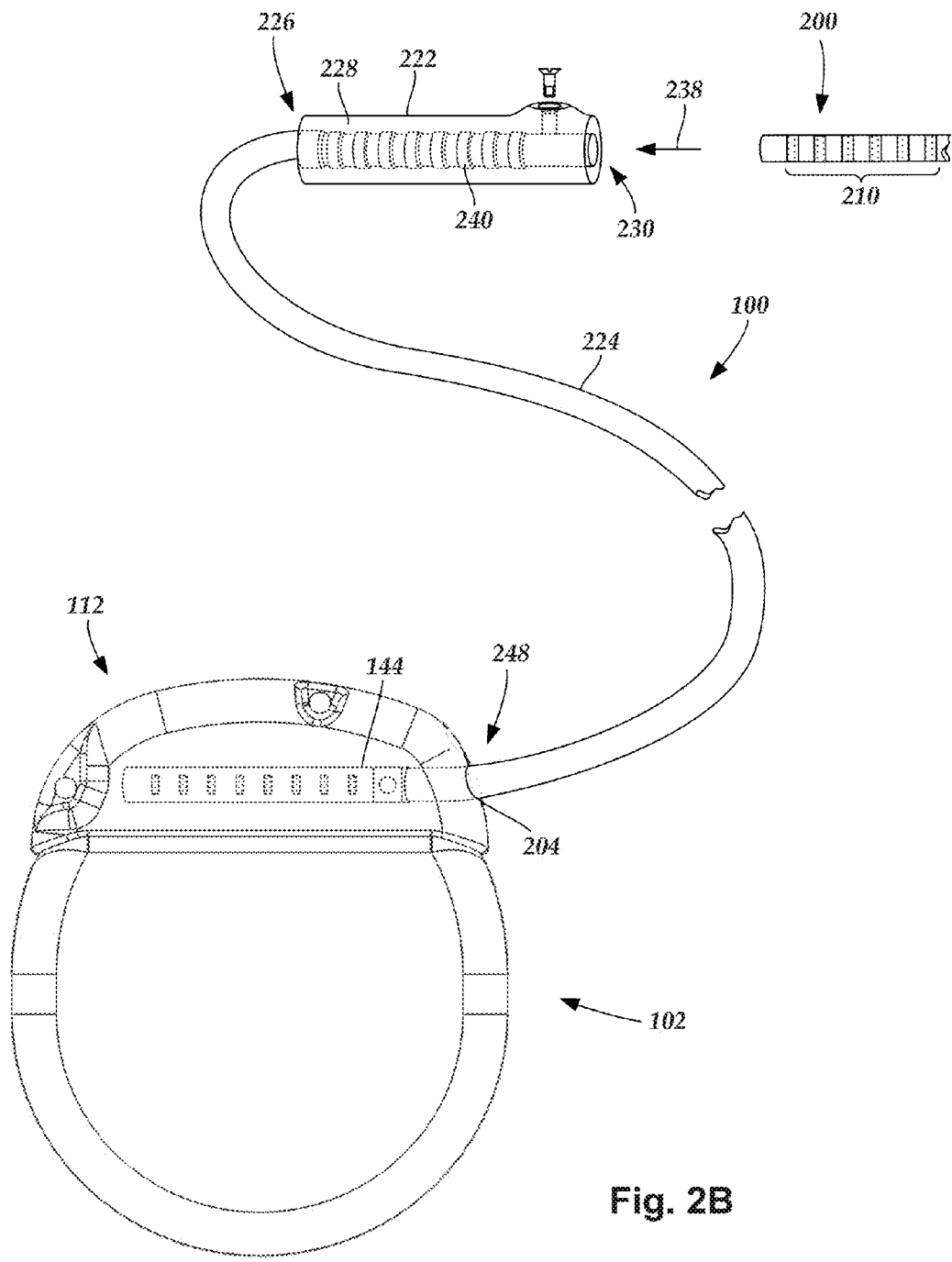
FIG. 2B is a schematic side view of one embodiment of a lead extension configured and arranged to electrically couple the elongated device of FIG. 2A to the control module of FIG. 1, according to the invention.

Terminals (e.g., 210 in FIGS. 2A-2B) are typically disposed along the proximal end of the one or more lead bodies 106 of the electrical stimulation system 100 (as well as any splitters, lead extensions, adaptors, or the like) for electrical connection to corresponding connector contacts (e.g., 214 in FIGS. 2A-2B). The connector contacts are disposed in connectors (e.g., 144 in FIGS. 1-2B; and 222 FIG. 2B) which, in turn, are disposed on, for example, the control module 102 (or a lead extension, a splitter, an adaptor, or the like). Conductor wires (not shown) extend from the terminals to the electrodes 134. Typically, one or more electrodes 134 are electrically coupled to each terminal. In at least some embodiments, each terminal is only connected to one electrode 134.

The conductor wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors may extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may also be one or more lumens (not shown) that open at, or near, the distal end of the one or more lead bodies 106, for example, for infusion of drugs or medication into the site of implantation of the one or more lead bodies 106. In at least one embodiment, the one or more lumens may be flushed continually, or on a regular basis, with saline, epidural fluid, or the like. In at least some embodiments, the one or more lumens can be permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, one or more of the lead bodies 106 of FIG. 1, one or more intermediate devices (e.g., a splitter, the lead extension 224 of FIG. 2B, an adaptor, or the like or combinations thereof), or a combination thereof.

The control module connector 144 defines at least one port into which a proximal end of the elongated device 200 can be inserted, as shown by directional arrows 212a and 212b. In FIG. 2A (and in other figures), the connector housing 112 is shown having two ports 204a and 204b. The connector housing 112 can define any suitable number of ports including, for example, one, two, three, four, five, six, seven, eight, or more ports.

The control module connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the control module 102 to the electrodes (134 of FIG. 1) disposed on the paddle body 104 of the lead 103. Examples of connectors in control modules are found in, for example, U.S. Pat. No. 7,244,150 and U.S. patent application Ser. No. 11/532,844, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., one of the lead bodies 106 of FIG. 1, a splitter, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144 (e.g., the ports 204*a* and 204*b* of FIG. 1), or to receive multiple elongated devices 200 (e.g., both of the lead bodies 106 of FIG. 1), or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

In at least some embodiments an insertion tool can be used to facilitate implantation of a paddle body at a target implantation site within a patient. Advancing the paddle body to the target stimulation location may involve passing one or more obstructions and, in the case of spinal cord stimulation, centering the paddle body along the center line of the spinal cord. As herein described, insertion tools are described that facilitate insertion of a paddle lead into a patient. U.S. Provisional Patent Application Ser. No. 61/738,624 describes other examples of paddle lead insertion tools and is incorporated herein by reference.

The insertion tools described herein couple to the paddle body of the paddle lead. In at least some embodiments, the insertion tools include one or more stylets for assisting in delivery and implantation of the paddle lead.

Figure 3A:
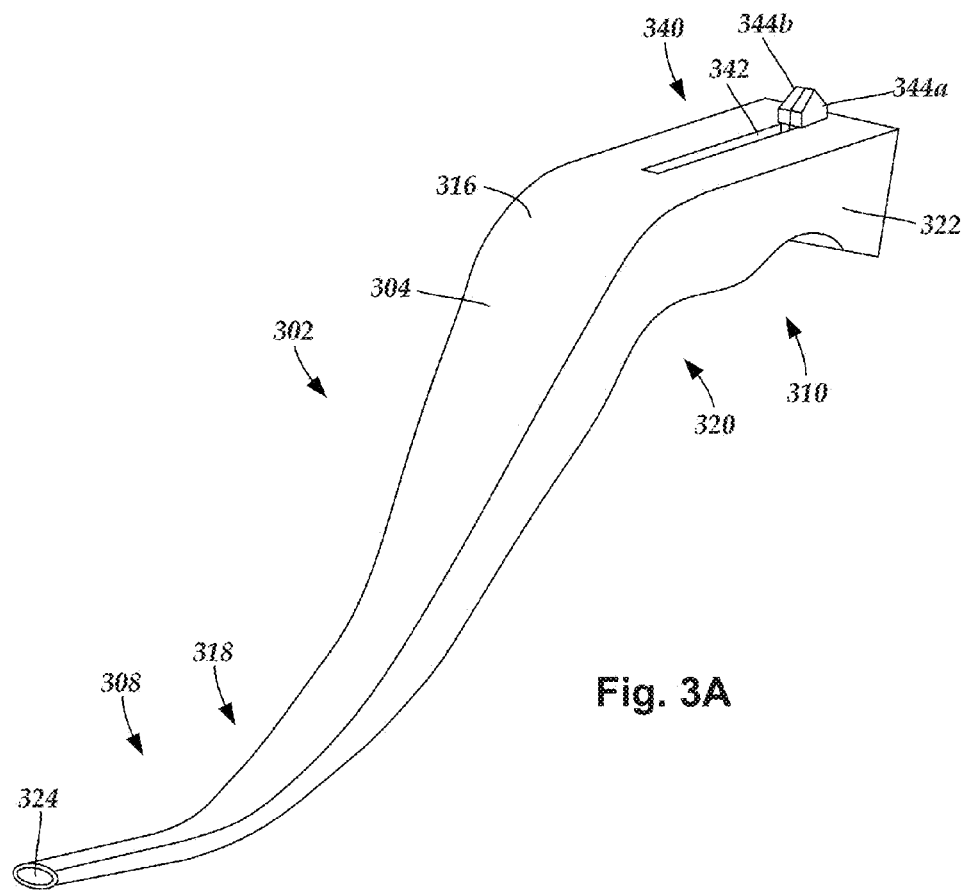
FIG. 3A is a schematic perspective view of one embodiment of an insertion tool for guiding a paddle lead to a target implantation site within a patient, according to the invention.
Figure 3B:
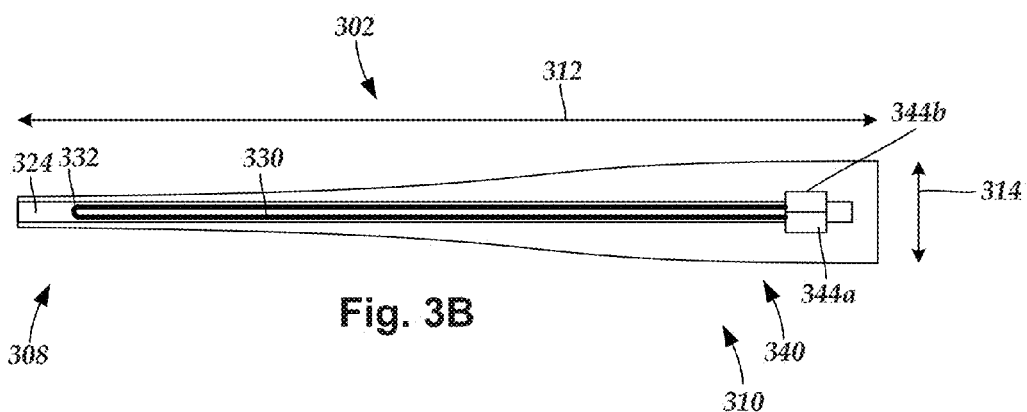
FIG. 3B is a schematic top view of one embodiment of the insertion tool of FIG. 3A, according to the invention.

FIGS. 3A and 3B illustrate one embodiment of an insertion tool 302 for guiding a paddle lead (see e.g., paddle lead 502 of FIG. 5A) into a target stimulation location within a patient. The insertion tool 302 includes an insertion tool body 304 having a receiving end portion 308 and a handling end portion 310. The insertion tool body 304 has a longitudinal length 312, a width 314, and an outer surface 316.

The insertion tool body 304 may have any suitable cross-section including, for example, a rectangular, round, or oval-shaped cross-section. In at least some embodiments, the cross-sectional shape of the insertion tool body 304 may change along the longitudinal length of the insertion tool body 304. In at least some embodiments, the width 314 is constant along the longitudinal length 312 of the insertion tool body 304. In at least some other embodiments, the width 314 varies along the longitudinal length 312 of the insertion tool body 304. In at least some embodiments, the handling end portion 310 of the insertion lead body 304 is wider than the receiving end portion 308 of the insertion tool body 304. For example, in at least some embodiments, the width 314 of the insertion tool body 304 tapers. It may be advantageous to design the insertion tool body 304 such that the handling end portion 310 is wider than the receiving end portion 308 because a larger handling end portion 310 may facilitate gripping of the insertion tool 302 by an operator, while a smaller receiving end portion 308 may facilitate insertion of the insertion tool 302 into the patient's body.

In at least some embodiments, the insertion tool body may be manufactured as an integrated structure (e.g., formed as a one-piece structure). In other embodiments, the insertion tool body 304 may be formed from multiple pieces that are coupled together during manufacture or by the user or any combination thereof. For example, insertion tool or the handling portion 310 of the insertion tool may be formed from two halves that are coupled together. In some embodiments, the receiving end portion 308 is made of a material such as silicone and has an end that is shaped (for example, shaped like an accordion) to fit into an end of the handling portion 310 during assembly of the insertion tool.

The insertion tool body 304 may include at least one curve along the longitudinal length 312 of the insertion tool body 304. In FIG. 3A, the insertion tool body 304 is shown having a first curve 318 and a second curve 320. It will be understood that insertion tool body 304 may include additional curves. The curve(s) may vary in number, size, or form. In FIG. 3A, the first curve 318 is shown positioned along the receiving end portion 308, while the second curve 320 may be positioned along the handling end portion 310. In at least some embodiment, the first curve 318 and the second curve 320 are oriented oppositely from one another such that the insertion tool body 304 forms an S-shaped configuration along the longitudinal length 312.

It may be advantageous to form the insertion tool body 304 into the S-shaped configuration for facilitating passing one or more anatomical structures (e.g., the inferior spinous process) while also allowing for a substantial angular entry into the target stimulation location, for example the epidural space, during insertion of the paddle lead. Moreover, the handling end portion 310 forming one part of the S-shaped configuration to enable a user's hand to be held away from an insertion site during an implantation procedure.

Optionally, the handling end portion 310 may include an insertion tool handle 322, dimensioned and sized to fit ergonomically within the hands of a user of the insertion tool 302. The insertion tool handle 322 may include recessed sections to comfortably accommodate a user's fingers and the thumb during applications. In some embodiments, cut outs may be provided on the insertion tool handle 322 for comfortable finger placement. In addition, a cross-sectional profile of the handling end portion 310 may be substantially rectangular with smoothed edges at the corners, making the insertion tool body 304 ergonomic and comfortable to store, hold, and operate. In at least some embodiments, the insertion tool handle 322 is integral with the insertion tool 302. In other embodiments, the insertion tool handle 322 is a separate structure for disposing on the insertion tool 302 by the user prior to (or during) use of the insertion tool 302.

The insertion tool 302 defines a stylet channel 324 (FIG. 3B) extending along the longitudinal length 312 of the insertion tool body 304. The stylet channel 324 receives one or more stylets 330. The stylet channel 324 may extend from the handling end portion 310 all the way to the receiving end portion 308. The stylet channel 324 may have any suitable cross-sectional profile including, for example, rectangular, round, oval-shaped, cruciform, star-shaped, or the like. In at least some embodiments, the cross-sectional profile of the stylet channel 324 varies along the length of the stylet channel 324.

A stylet wire 330 extends from a first actuator handle 344a, loops around at a distal end portion 332, and extends back to a second actuator handle 344b. In at least some embodiments, the stylet wire 330 can be viewed as forming a 180 degree loop. The stylet wire 330 is disposed within the stylet channel 324 with the distal end portion 332 disposed along the receiving end portion 308 of the insertion tool body 304.

Structurally, the stylet wire 330 is an elongate, flexible wire with enough rigidity to guide a paddle lead. The stylet wire 330 can be formed from any suitable materials, such as, for example, nitinol (a nickel titanium alloy with shape memory and superelastic characteristics), stainless steel, or the like. In at least some embodiments, the stylet wire is radiopaque (e.g., nitinol) so that the wire can be viewed fluoroscopically.

The stylet wire 330 remains at least partially disposed within the stylet channel 324 and slides along the stylet channel 324 relative to the insertion tool body 304. In some embodiments, the stylet wire 330 is permanently fixed to the insertion tool 302. In other embodiments, the stylet wire 330 is removable from the insertion tool 302.

The insertion tool 302 includes an actuator assembly 340 for controlling movement of the stylet wire 330 along the stylet channel 324 relative to the insertion tool body 304 along the longitudinal length 312 of the insertion tool body 304. For example, the actuator assembly 340 controls movement of the stylet wire 330 relative to the insertion tool body 304 when transitioning of the stylet wire 330 between retracted and extended positions.

The actuator assembly 340 can include an opening or slot defined along the outer surface 316 of the insertion tool body 304, referred to as an actuator slit 342. Two actuator handles 344a, 344b are disposed over the actuator slit 342 and slide along the actuator slit 342. In some embodiments, the insertion tool includes a separate actuator slit for each actuator handle 344a, 344b. Each of the actuator handles 344a, 344b is attached to a different end of the stylet wire 330. The actuator handles 344a, 344b can be operated independently of each other or operated together and can be used, when operated independently, to steer the paddle lead to the right or left of the receiving end portion 308 of the insertion tool 302 as described below.

Figure 4A:
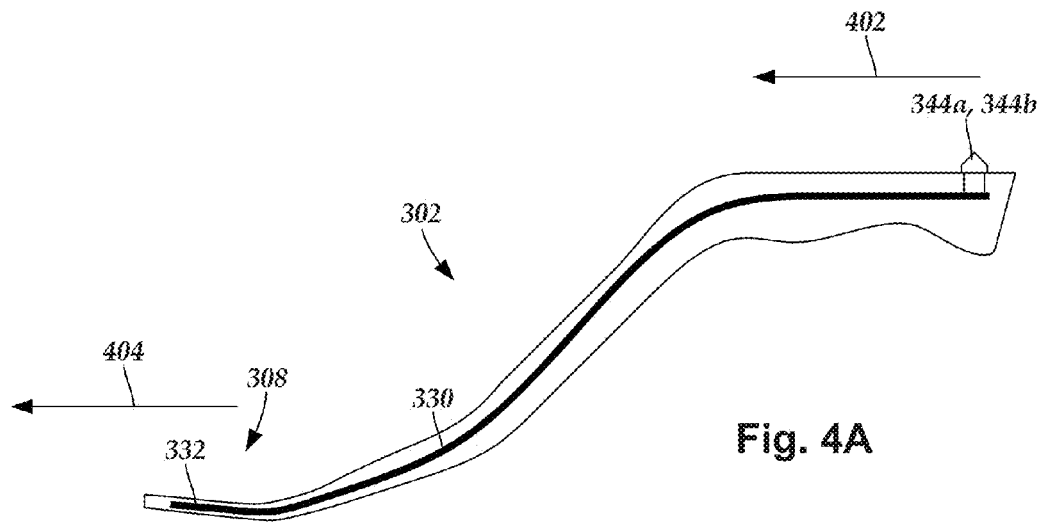
FIG. 4A is a schematic longitudinal cross-sectional view of one embodiment of a stylet disposed in the insertion tool of FIG. 3A, where the stylet is in a retracted position, according to the invention.
Figure 4B:
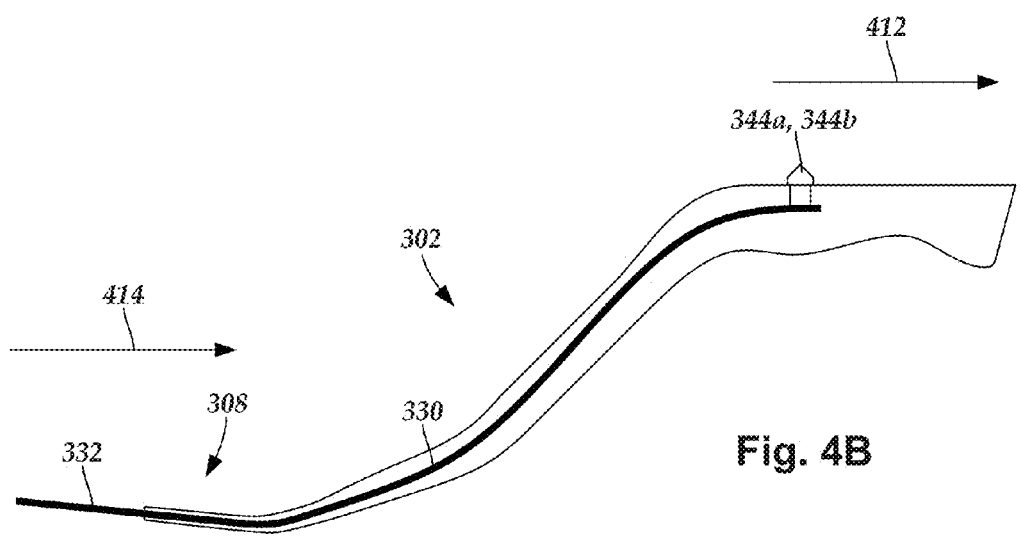
FIG. 4B is a schematic longitudinal cross-sectional view of one embodiment of a stylet disposed in the insertion tool of FIG. 3A, where the stylet is in an extended position with the stylet extending outwardly from a receiving end portion of the insertion tool, according to the invention.

FIGS. 4A-4B show one embodiment of movement of the stylet wire 330 within the insertion tool 302. FIG. 4A is a side view of one embodiment of the insertion tool 302 with the stylet wire 330 in a retracted position. FIG. 4B is a side view of the insertion tool 302 with the stylet wire 330 in an extended position. In FIG. 4A, the movement of the stylet wire 330 with respect to the insertion tool 302 from a retracted position to an extended position is shown by arrows 402 and 404. As shown in FIG. 4B, when the actuator handle 344a, 344b is moved in the direction of the arrow 412, the distal end portion 332 of the stylet wire 330 retracts in the direction of the arrow 414. In at least some embodiments, extension and retraction limits of the stylet wire 330 may be realized through the length of the actuator slit 342.

The placement of a medical device, such as a paddle lead, during an implantation procedure includes advancing the paddle lead to the patient's epidural space. FIGS. 5A-5D illustrate the use of the insertion tool 302 to implant a paddle lead. FIGS. 5A-5D illustrate a paddle lead 502 accompanied by a portion of the receiving end portion 308, stylet channel 324, stylet wire 330, and actuator handles 344a, 344b of the insertion tool 302. The paddle lead 502 includes a paddle body 504, and first and second lead bodies 506a and 506b, respectively, coupled to the paddle body 504. Electrodes 508 are shown disposed along a major surface of the paddle body 504. The paddle lead 502 may include any suitable number of lead bodies and any suitable number of electrodes 508. A stylet lumen 510 is defined within the paddle body 504 along its longitudinal axis. The stylet lumen 510 receives the distal end portion 332 of the stylet wire 330.

In FIGS. 5A-5D, the electrodes 508 are shown disposed into two columns, both having equal number of electrodes 508, such that the stylet lumen 510 occupies a space between the two columns of the electrodes 508. In at least some embodiments, the stylet lumen 510 extends parallel with the columns of electrodes 508. In at least some embodiments, the stylet lumen 510 is disposed between adjacent columns of electrodes 508. In at least some embodiments, the stylet lumen 510 is defined along the paddle body 504 such that an equal number of columns of electrodes 508 are disposed on each side of the stylet lumen 510. Such an arrangement of the stylet lumen 510 within the paddle body 504 may allow the insertion tool 302 to impart a considerably balanced and enhanced maneuvering ability to position the lead effectively during operations.

Figures 5A, 5B:
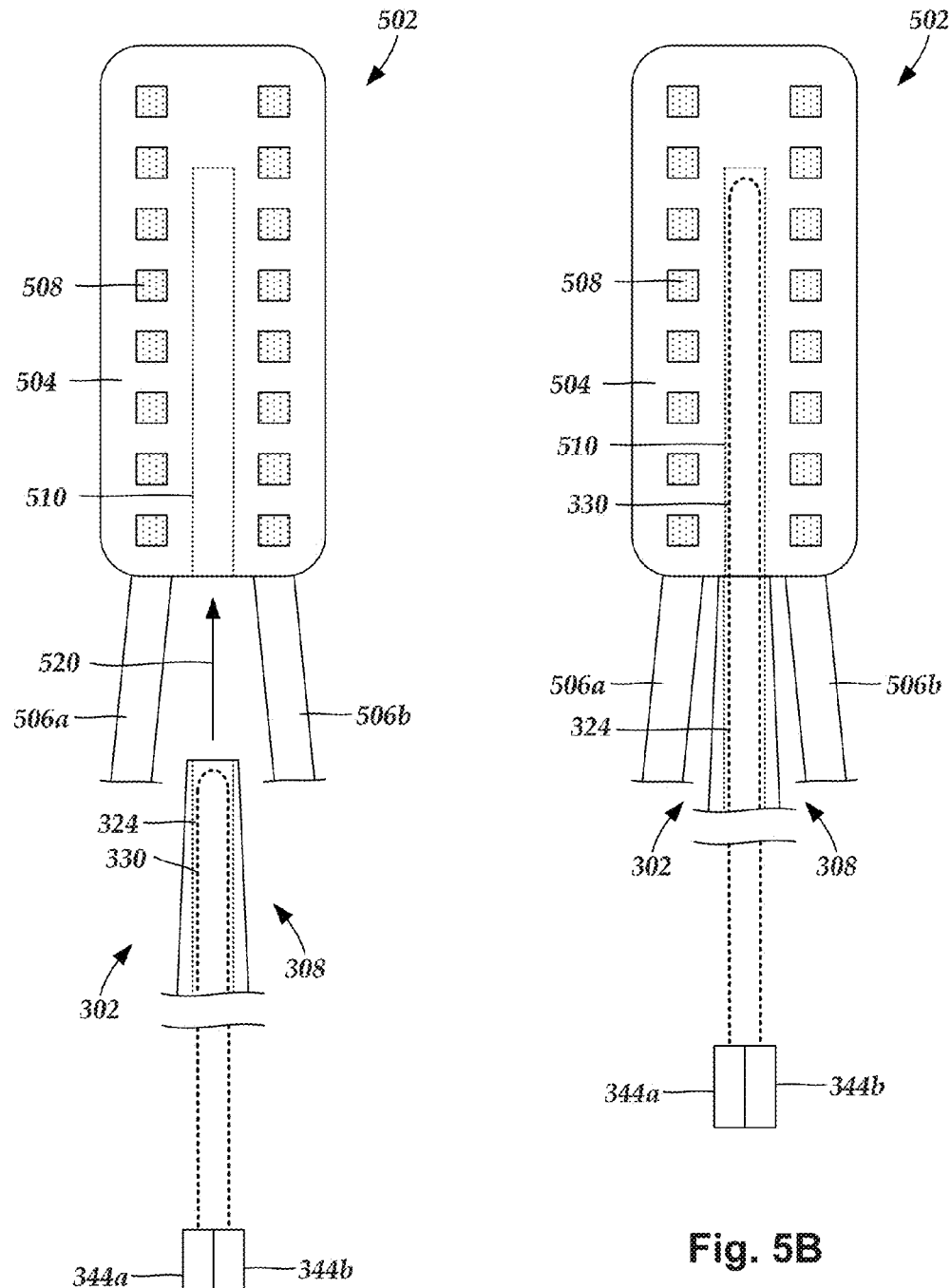
FIG. 5A is a schematic top view of one embodiment of a portion of a paddle lead and a portion of the insertion tool of FIG. 3A with a stylet lumen disposed in a paddle body of the paddle lead, according to the invention.
FIG. 5B is a schematic top view of one embodiment of the portion of the paddle lead and the portion of the insertion tool of FIG. 5A with the stylet of the insertion tool inserted into the stylet lumen of the paddle body, according to the invention.

FIG. 5A illustrates the insertion tool 302 disposed in proximity to the paddle lead 502 with the stylet wire 330 in the retracted position. As shown by arrow 520, a user can position the insertion tool 302 outside an opening of the stylet lumen 510 and insert a portion of the stylet wire 330 of the insertion tool 302 into the stylet lumen 510 of the paddle body 504. In at least some embodiments, the insertion tool can abut the paddle body 504. FIG. 5B shows the insertion tool 302 abutting the paddle body 504 and the stylet wire 330 in an extended position with the stylet wire 330 extended into the stylet lumen 510.

Once the stylet wire 330 is inserted into the paddle lead 502, a user may use the insertion tool 302 to guide, steer, and position, the paddle lead 502 at a target stimulation location within a patient. Once the paddle body 504 of the paddle lead 502 is positioned, the stylet wire 330 may be removed from the paddle body 504. In at least some embodiments, the stylet wire 330 is removed from the paddle body 504 without moving the paddle body 504. In which case, removal of the insertion tool 302 can be performed without disrupting the placement of the paddle body 504.

Figure 5C:
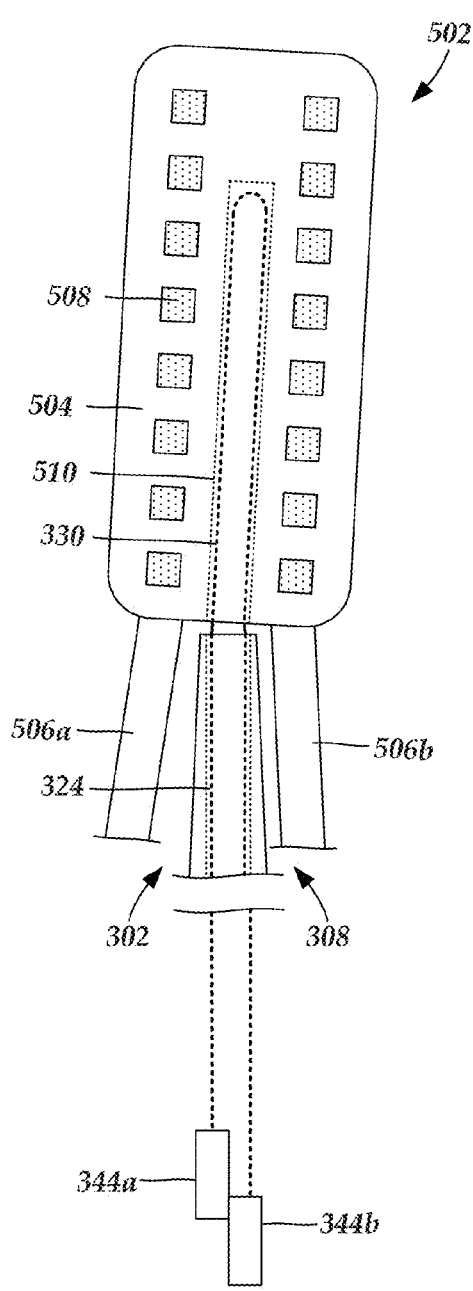
FIG. 5C is a schematic top view of one embodiment of the portion of the paddle lead and the portion of the insertion tool of FIG. 5B with the stylet of the insertion tool being used to steer the paddle body to the right, according to the invention.

FIG. 5C illustrates steering of the paddle lead 502 using the stylet wire 330 and the actuator handles 344a, 344b. In the illustration, the second actuator handle 344b is pulled back relative to the first actuator handle 344a. This cases the stylet wire 330 to pull the paddle lead 502 to the right. The opposite relative arrangement of handles 344a, 344b can be used to pull the paddle lead 502 to the left. The wire stylet 330 is selected of a material and size that it is sufficiently flexible to bend in response to the actuator handles 344a, 344b, but also sufficiently stiff to cause the paddle lead to move to the right or left.

Figure 5D:
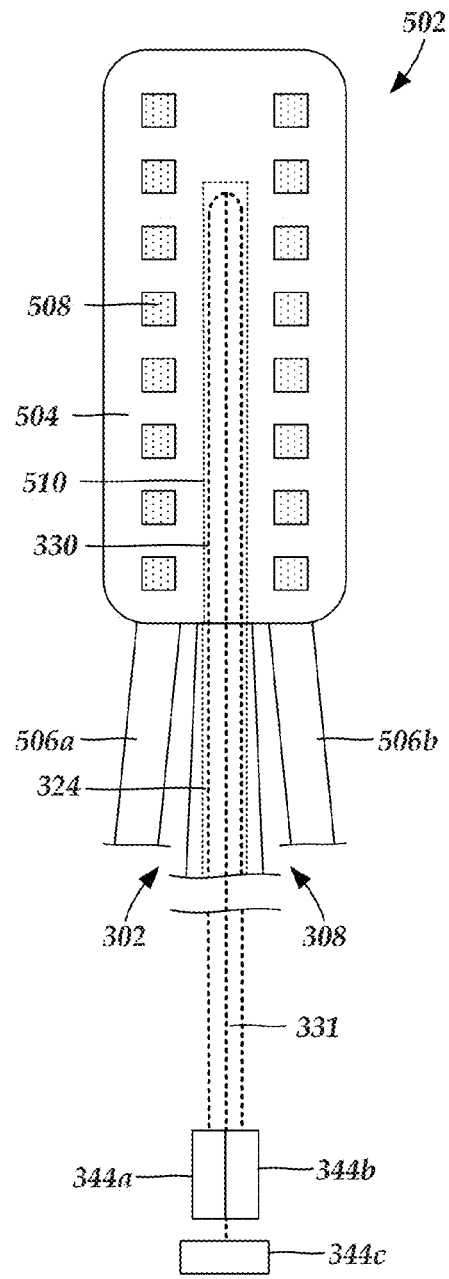
FIG. 5D is a schematic top view of another embodiment of a portion of a paddle lead and a portion of an insertion tool where the stylet includes a rotational wire, according to the invention.

FIG. 5D illustrates another embodiment of the insertion tool 302 which incorporates a rotational wire 331 that is attached (e.g., welded, soldered, or the like) to the stylet wire 330 and to a third actuator handle 344c. The rotational wire 331 can be used to rotate the paddle lead clockwise or counterclockwise relative to the rotational wire 331. This adds a further degree of freedom in positioning the lead body. The actuator handle 344c may be a sliding button or a rotating wheel or any other suitable mechanism to generate rotation of the rotational wire 331.

FIGS. 6A-6E illustrate another insertion tool 602 for implantation of a paddle lead 502 (see, FIGS. 6D and 6E) with electrodes 508 on a paddle body 504 and one or more lead bodies 506a, 506b attached to the paddle body. Similar to the insertion tool 302 of FIGS. 3A-4B, insertion tool 602 includes an insertion tool body 604, a receiving end portion 608, a handling end portion 620, an outer surface 616, one or more curves 618, 620, an insertion tool handle 622, a stylet channel 624, an actuator assembly 640, an actuator slit 642, and an actuator handle 644. Unless otherwise indicated the properties, materials, and manufacture of insertion tool 602 and its parts are the same as those for insertion tool 302 and its parts.

Figure 6D:
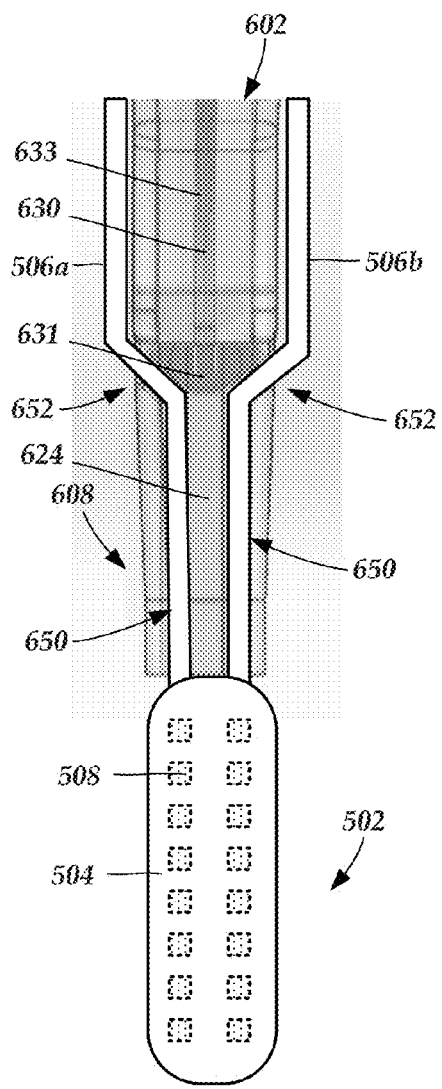
FIG. 6D is a schematic top view of the receiving end portion of the insertion tool of FIG. 6A and a paddle lead in an implantation position, according to the invention.

The configuration of the receiving end portion 608, as illustrated in more detail in FIGS. 6B and 6C, is different from the previous embodiment. The receiving end portion 608 includes a stylet channel 624 and one or more lead body channels 650 that are adjacent and preferably open to the stylet channel 624. The lead body channels 650 terminate in exit openings 652 spaced away from the distal end of the receiving end portion 608. As illustrated in FIG. 6D, the lead bodies 506a, 506b of the paddle lead 502 are each inserted into one of the lead body channels 650 and a portion of the lead body extends out of the corresponding exit opening 652. In addition, for each lead body channel 650 there is an exit slit 654 running from the distal end of the receiving end portion 608 to the corresponding exit opening 652. Each exit slit 654 extends from the outer surface 616 of the insertion tool 602 to the corresponding lead body channel 650. The exit slit 654 typically remains closed and is resistant to release of the lead body 506a, 506b from the lead body channel 650, but when sufficient lateral force is applied from the stylet, as described below, the lead body 560a, 560b can be pushed out of the lead body channel 650 through the exit slit 654 and out of the insertion tool 602 entirely.

The insertion tool 602 includes a stylet 630. The illustrated embodiment of the stylet 630 includes a head 631 attached to a shaft 632. It will be understood, however, that alternative embodiments of the stylet 630 can include a longer head 631 or even a head that extends along the entire length of the stylet so that there is no shaft.

The head 631 of the stylet 630 is wider than the separation distance between the lead body channels 650 and is preferably nearly as wide as the receiving end portion 608 at its distal end. The head 631 may have a tapered or arrow-like shape, as illustrated in FIG. 6D, to facilitate pushing the lead bodies 506a, 506b out of the lead body channels 650 with little or no damage to the lead bodies 506a, 506b.

Figure 6E:
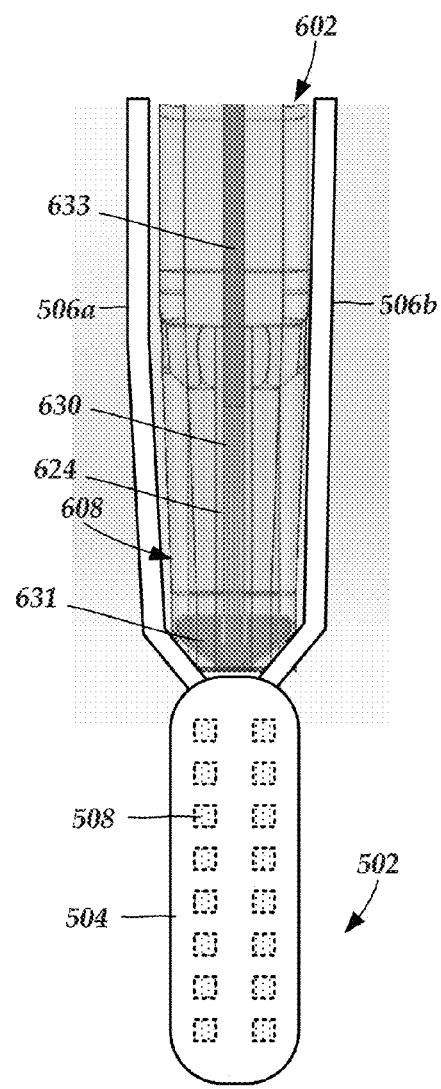
FIG. 6E is a schematic top view of the receiving end portion of the insertion tool of FIG. 6A and a paddle lead in a position with the paddle lead released from the insertion tool, according to the invention.

FIGS. 6D and 6E illustrate the receiving end portion 608 of the insertion tool 602 and a paddle lead 502 at two different stages of the implantation of the paddle lead. FIG. 6D illustrates the arrangement during the insertion of the paddle lead into patient tissue and steering of the paddle lead to the target implantation site. In the arrangement of FIG. 6D, the lead bodies 506a, 506b are inserted into corresponding lead body channels 650 so that the paddle lead 502 is held by the receiving end portion 608 of the insertion tool 602. In this position, the insertion tool 602 can be used to guide the paddle lead 502 to the target implantation site. The lead bodies 506a, 506b exit the receiving end portion 608 through the exit openings 652. The stylet 630 is in a first position which, in the illustrated embodiment, is a retracted position relative to the lead bodies 506a, 506b.

FIG. 6E illustrates the arrangement after location of the paddle lead at the target implantation site and the disengagement of the insertion tool 602 from the paddle lead 502. The stylet 630 has been advanced to a second portion which, in the illustrated embodiment, is an extended position relative to the lead bodies 506a, 506b. During the transition from the first position to the second position, the head 631 of the stylet 630 pushes the lead bodies 506a, 506b out of the lead body channels 650 through the exit slits 654 (see, FIGS. 6B and 6C) and out of the insertion tool 602. The insertion tool 602 can then be removed leaving the paddle lead 502 implanted at the target implantation location.

In some embodiments, the head 631 pushes the entire lead bodies 506a, 506b out of the insertion tool 602. In other embodiments, a small portion of the lead bodies 506a, 506b may remain in the insertion tool 602, but these small portions are preferably easily removed as the insertion tool 602 is withdrawn so that the position of the paddle lead 502 in the patient is not disturbed. In some embodiments, the head 631 of the stylet 630 remains within the receiving end portion 608 when in the first and second positions, as illustrated in FIGS. 6D and 6E. In other embodiments, the head 631 of the stylet 630 (or a portion of the head) may exit the receiving end portion 608 during the implantation process.

In an alternative embodiment (not shown), the head of the stylet is reversed with the point of the head directed back toward the handle of the insertion tool. In these embodiments, the first position is extended (similar to FIG. 6E) with the lead bodies disposed in the lead body channel behind the head of the stylet. The stylet can then be retracted to the second position (similar to FIG. 6D) pushing the lead bodies out of the lead body channels to release the lead bodies from the insertion tool.

Other embodiments of an insertion tool use a paddle envelope to hold the paddle lead during implantation and then release the paddle lead after it has been delivered to the desired implantation site. The paddle envelope extends from the receiving end portion and may be coupled to a stylet or responsive to the operation of a stylet. The insertion tools described with respect to FIGS. 7A-10B are similar to insertion tools 302 and 602 except that the insertion tool end portion has a paddle envelope. All other design considerations, materials, and manufacturing methods of the previously described insertion tools are applicable to those described with respect to FIGS. 7A-10B.

Figure 7A:
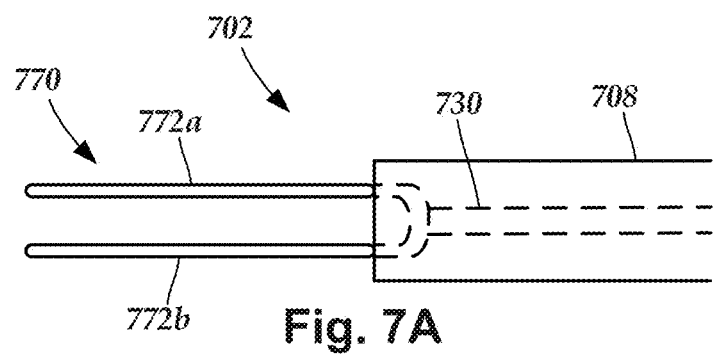
FIG. 7A is a schematic side view of one embodiment of a receiving end portion of an insertion tool with a paddle envelope, according to the invention.
Figure 7B:
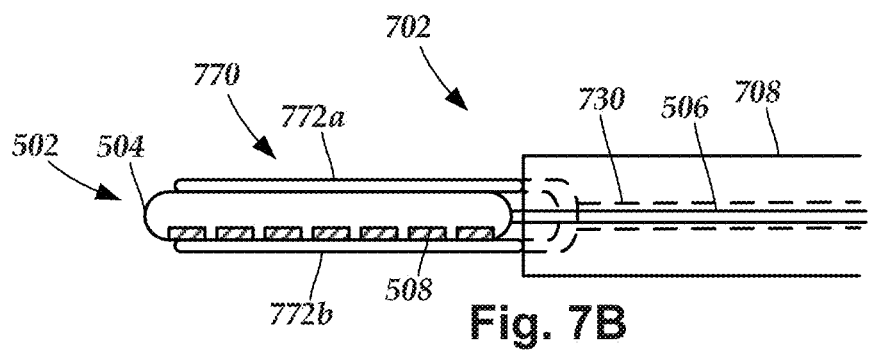
FIG. 7B is a schematic side view of the receiving end portion of FIG. 7A with a paddle lead disposed therein, according to the invention.

FIGS. 7A and 7B illustrate one example of a paddle envelope 770 of an insertion tool 702. The paddle envelope 770 extends from the receiving end portion 708 of the insertion tool 702 and contains two or more envelope elements 772a, 772b. The paddle envelope 770 is coupled to a stylet 730 that can be used to extend or retract the paddle envelope. The paddle envelope 770 can be refracted into the receiving end portion 708 or over the receiving end portion.

The paddle envelope 770 is extended to engage the paddle body 504 of the paddle lead 502 with one or more lead bodies 506 extending to either side of the receiving end portion 708 of the insertion tool 702, as illustrated in FIG. 7B. The paddle envelope 770 can be retracted to release the paddle lead 502 when it has been delivered to the target implantation site.

The two envelope elements 772a, 772b are preferably made of a material that is sufficiently flexible so as to reduce or avoid damage to patient tissue or the paddle body 504 or electrodes 508 on the paddle body. The envelope elements 772a, 772b are also preferably sufficiently rigid to hold the paddle body 504 during implantation. The envelope elements can be made of any suitable, biocompatible material including, but not limited to, silicone, polyurethane, and the like.

In some embodiments, the envelope elements are made of alternating (either laterally or longitudinally) regions of polymeric material (such as silicone) with different durometers. The lower durometer material can provide flexibility and the higher durometer material can provide rigidity. In other embodiments, a wire (e.g., a nitinol wire) or other rigid element may be encased (e.g., overmolded by polymer material or covered by heat shrink material) by a pliable material to form the envelope elements 772a, 772b. In some embodiments, a compressive force to hold the paddle body 504 during implantation may be obtained by arranging the envelope elements 772a, 772b so that in their free state the one or both elements are angled toward the other.

Figure 7C:
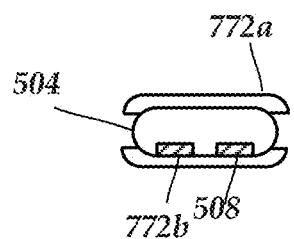
FIG. 7C is a schematic end view of one embodiment of a paddle envelope with a paddle lead, according to the invention.
Figure 7D:
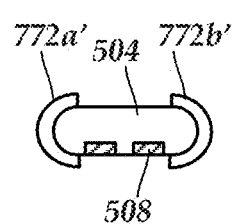
FIG. 7D is a schematic end view of another embodiment of a paddle envelope with a paddle lead, according to the invention.
Figure 7E:
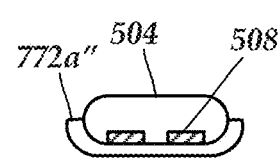
FIG. 7E is a schematic end view of a third embodiment of a paddle envelope with a paddle lead, according to the invention.

FIGS. 7C-7E illustrate three different paddle envelope embodiments 770, 770', 770" with different sites of engagement of the paddle lead 502. The embodiment of FIG. 7C has two envelope elements 772a, 772b that engage the top and bottom surfaces of the paddle body 504. The embodiment of FIG. 7D has two envelope elements 772a', 772b' that engage the side surfaces of the paddle body 504 and may extend partially to the top surface or bottom surface or both. The embodiment of FIG. 7E has a single envelope elements 772" that engages the bottom surface (or alternatively, the top surface) of the paddle body 504. This single envelope element 772" may grip the paddle body 504 to maintain contact during implantation of the paddle lead, but such a grip is releasable upon retraction of the envelope element 772" using the stylet 730 (see, FIG. 7A). Alternatively, the envelope element 772" may be primarily a platform upon which the paddle body 504 is rests during implantation.

Figure 8:
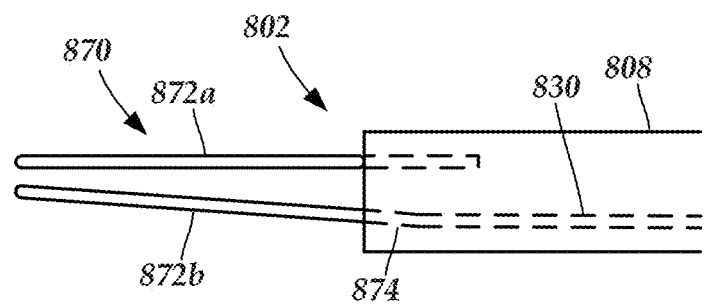
FIG. 8 is a schematic side view of a second embodiment of a receiving end portion of an insertion tool with a paddle envelope, according to the invention.

FIG. 8 illustrates another embodiment of an insertion tool 802 with a paddle envelope 870 extending from the receiving end portion 808 of the insertion tool. This paddle envelope 870 has a stationary envelope element 872a (which is optionally integrally formed with the receiving end portion 808) that is attached to the receiving end portion 808 and remains stationary relative to the receiving end portion. The paddle envelope also includes a retractable envelope element 872b. The illustrated embodiment shows the retractable element 872b with a bend 874 so that in its free state it will be angled toward the stationary envelope element 872a, but such a bend is optional (i.e., the retractable element 872b can be straight) or the stationary envelope element 872a can be bent. Unless otherwise indicated, a bend in one or more envelope elements can be incorporated in any of the other embodiments illustrated in FIGS. 7A-10B.

The retractable envelope element 872b can be extended to hold a paddle body between the envelope elements 872a, 872b. The retractable envelope element 872b can be refracted using the stylet 830 to release the paddle body at the target implantation site.

Figure 9A:
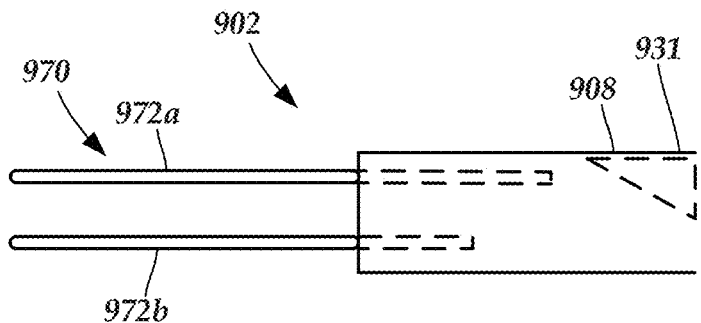
FIG. 9A is a schematic side view of a third embodiment of a receiving end portion of an insertion tool with a paddle envelope, according to the invention.
Figure 9B:
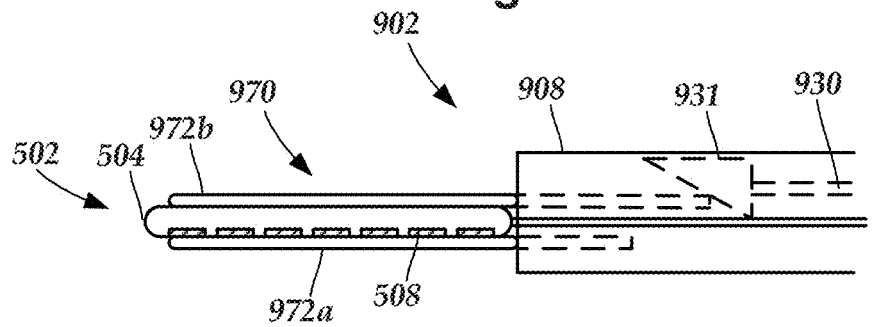
FIG. 9B is a schematic side view of the receiving end portion of FIG. 9A with a paddle lead disposed therein, according to the invention.

FIGS. 9A and 9B illustrate another embodiment of an insertion tool 902 with a paddle envelope 970 extending from the receiving end portion 908 of the insertion tool. This paddle envelope 970 has a stationary envelope element 972a and a movable envelope element 972b. The movement of envelope element 972b is lateral with respect to the major surfaces of the paddle lead include the major surface with the electrodes disposed thereon. In addition, the insertion tool 902 includes a stylet 930 with a head 931 attached to the stylet. In the open position of FIG. 9A, the stylet 930 and stylet head 931 are retracted and the envelope elements 972a, 972b are separated to allow insertion of a paddle body 504 of a paddle lead 502 between the envelope elements. In the closed position of FIG. 9B, the stylet 930 is advanced so that the head 931 causes the movable envelope element 972b to engage the paddle body 504 and hold the paddle body 504 between the envelope elements 972a, 972b during the implantation procedure. Once implanted, the stylet 930 can be retracted to allow the movable envelope element 972b to move away from stationary envelope element 972a (see, e.g., FIG. 9A) and release the paddle body 504.

Figure 10A:
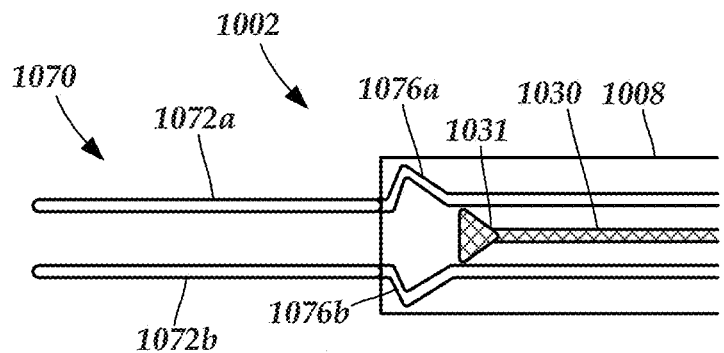
FIG. 10A is a schematic side view of a fourth embodiment of a receiving end portion of an insertion tool with a paddle envelope in an open position, according to the invention.
Figure 10B:
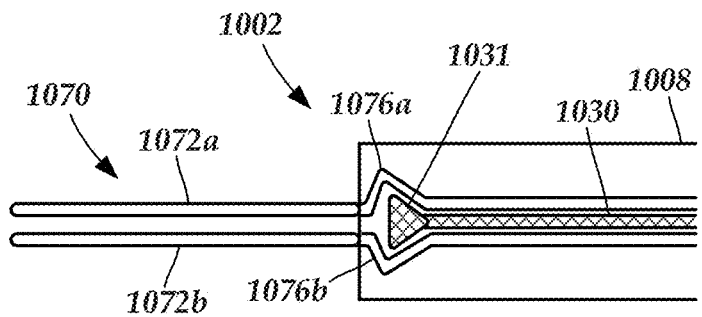
FIG. 10B is a schematic side view of the receiving end portion of FIG. 10A in a closed position, according to the invention.

FIGS. 10A and 10B illustrate another embodiment of an insertion tool 1002 with a paddle envelope 1070 extending from the receiving end portion 1008 of the insertion tool. This paddle envelope 1070 has two envelope elements 1072a, 1072b. In addition, the insertion tool 1002 includes a stylet 1030 with a head 1031 attached to the stylet. Each of the envelope element 1072a, 1072b has a bent or curved region 1076a, 1076b that, at least in the closed position of FIG. 10B, fits around the head 1031 of the stylet 1030. In the open position of FIG. 10A, the stylet 1030 is retracted and the envelope elements 1072a, 1072b are separated by the head 1031 of the stylet 1030 to allow insertion of a paddle body of a paddle lead between the envelope elements. In the closed position of FIG. 10B, the stylet 1030 is advanced so that the head 1031 is within the regions 1076a, 1076b with the two envelope element 1072a, 1072b drawn together (using a spring or any other mechanism) to engage the paddle body and hold the paddle body between the envelope elements 1072a, 1072b during the implantation procedure. Once implanted, the stylet 1030 can be refracted to allow the envelope elements 1072 a, 1072b to move away from each other (see, e.g., FIG. 10A) and release the paddle body.

In alternative embodiments to that of FIGS. 10A and 10B, only one of the envelope elements has a bent or curved region and is moved by the stylet. The other envelope element remains stationary, similar to the embodiment of FIGS. 9A and 9B.

Figure 11A:
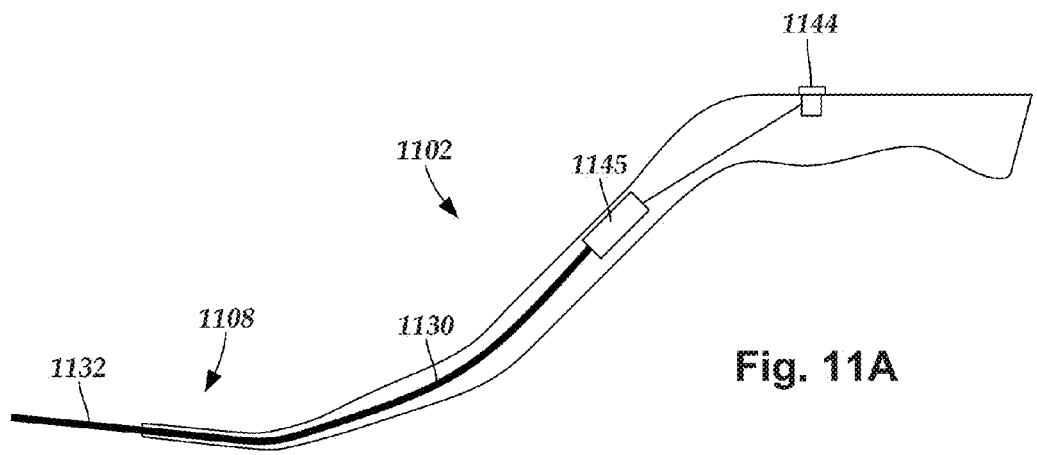
FIG. 11A is a schematic longitudinal cross-sectional view of one embodiment of a stylet disposed in an insertion tool with a stylet holding mechanism where the stylet is in an extended position, according to the invention.
Figure 11B:
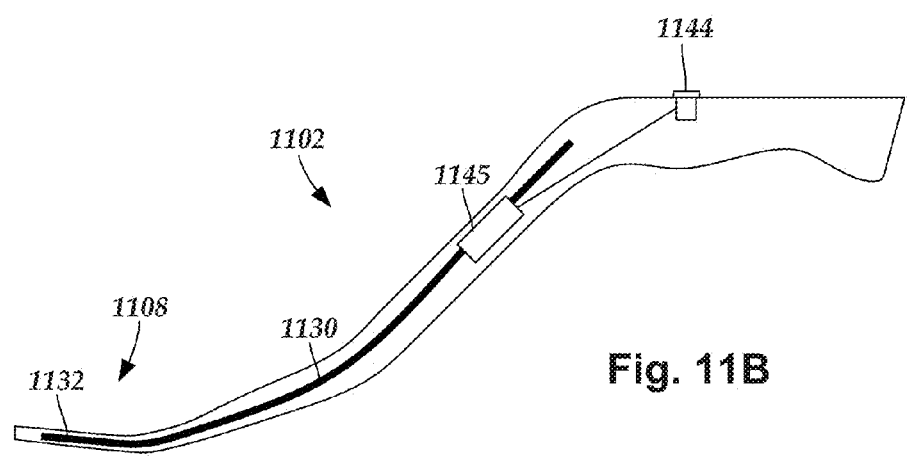
FIG. 11B is a schematic longitudinal cross-sectional view of one embodiment of a stylet disposed in the insertion tool of FIG. 11A with the stylet is in a refracted position, according to the invention.

FIGS. 11A and 11B illustrate an alternative stylet retraction mechanism that can be incorporated in any of the embodiments described herein (particularly, the embodiments illustrated in FIGS. 6A-10B) or in any of the insertion tools described in U.S. Provisional Patent Application Ser. No. 61/738,624. An insertion tool 1102 has a receiving end portion 1108, a stylet 1130, and a stylet end portion 1132. The insertion tool 1102 also includes a button 1144 that, when actuated operates a stylet holding mechanism 1145. The stylet holding mechanism 1145 can incorporate a spring or other arrangement that holds the stylet in place, but can be released to retract the stylet. For example, the stylet holding mechanism can incorporate a spring that is compressed and attached to the stylet, as illustrated in FIG. 11A. When the button 1144 is actuated the compression on the spring is released and the spring relaxes to its uncompressed state and, as a result, retracts the stylet, as illustrated in FIG. 11B. It will be understood that a similar mechanism can be used to extend the stylet rather than retract the stylet. Moreover, it will be understood that the stylet holding mechanism described herein can be used with any of the stylets described herein to transition the stylet from a first position to a second position.

Figure 12:
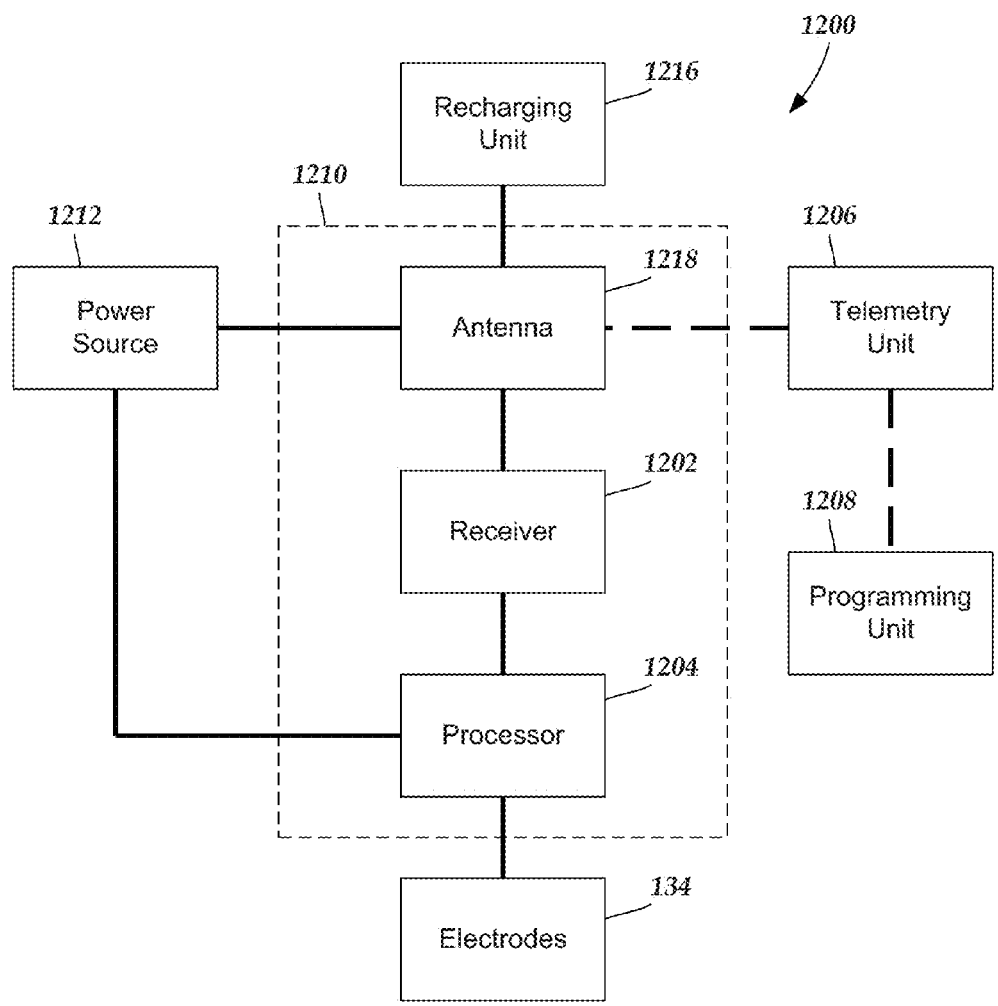
FIG. 12 is a schematic overview of one embodiment of components of a stimulation system, including an electronic subassembly disposed within a control module, according to the invention.

FIG. 12 is a schematic overview of one embodiment of components of an electrical stimulation system 1200 including an electronic subassembly 1210 disposed within a control module. It will be understood that the electrical stimulation system can include more, fewer, or different components and can have a variety of different configurations including those configurations disclosed in the stimulator references cited herein.

Some of the components (for example, power source 1212, antenna 1218, receiver 1202, and processor 1204) of the electrical stimulation system can be positioned on one or more circuit boards or similar carriers within a sealed housing of an implantable pulse generator, if desired. Any power source 1212 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1218 or a secondary antenna. The external power source can be in a device that is mounted on the skin of the user or in a unit that is provided near the user on a permanent or periodic basis.

If the power source 1212 is a rechargeable battery, the battery may be recharged using the optional antenna 1218, if desired. Power can be provided to the battery for recharging by inductively coupling the battery through the antenna to a recharging unit 1216 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1204 is generally included to control the timing and electrical characteristics of the electrical stimulation system. For example, the processor 1204 can, if desired, control one or more of the timing, frequency, strength, duration, and waveform of the pulses. In addition, the processor 1204 can select which electrodes can be used to provide stimulation, if desired. In some embodiments, the processor 1204 may select which electrode(s) are cathodes and which electrode(s) are anodes. In some embodiments, the processor 1204 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1208 that, for example, allows modification of pulse characteristics. In the illustrated embodiment, the processor 1204 is coupled to a receiver 1202 which, in turn, is coupled to the optional antenna 1218. This allows the processor 1204 to receive instructions from an external source to, for example, direct the pulse characteristics and the selection of electrodes, if desired.

In one embodiment, the antenna 1218 is capable of receiving signals (e.g., RF signals) from an external telemetry unit 1206 which is programmed by a programming unit 1208. The programming unit 1208 can be external to, or part of, the telemetry unit 1206. The telemetry unit 1206 can be a device that is worn on the skin of the user or can be carried by the user and can have a form similar to a pager, cellular phone, or remote control, if desired. As another alternative, the telemetry unit 1206 may not be worn or carried by the user but may only be available at a home station or at a clinician's office. The programming unit 1208 can be any unit that can provide information to the telemetry unit 1206 for transmission to the electrical stimulation system 1200. The programming unit 1208 can be part of the telemetry unit 1206 or can provide signals or information to the telemetry unit 1206 via a wireless or wired connection. One example of a suitable programming unit is a computer operated by the user or clinician to send signals to the telemetry unit 1206.

The signals sent to the processor 1204 via the antenna 1218 and receiver 1202 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1200 to cease operation, to start operation, to start charging the battery, or to stop charging the battery. In other embodiments, the stimulation system does not include an antenna 1218 or receiver 1202 and the processor 1204 operates as programmed.

Optionally, the electrical stimulation system 1200 may include a transmitter (not shown) coupled to the processor 1204 and the antenna 1218 for transmitting signals back to the telemetry unit 1206 or another unit capable of receiving the signals. For example, the electrical stimulation system 1200 may transmit signals indicating whether the electrical stimulation system 1200 is operating properly or not or indicating when the battery needs to be charged or the level of charge remaining in the battery. The processor 1204 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An insertion tool for a paddle lead, the paddle lead comprising a paddle body and at least one lead body extending from the paddle body, the insertion tool comprising:

an insertion tool body comprising a receiving end portion, a handling end portion, an outer surface, and a longitudinal length, wherein the receiving end portion comprises a distal end, two lead body channels, two opposing exit openings disposed proximal to the distal end on opposite sides of the receiving end portion with each exit opening extending inwardly from the outer surface to a one of the two lead body channels, and two opposing slits with each slit extending from the distal end to a one of the two exit openings and extending inwardly from the outer surface to a one of the lead body channels, wherein each of the two lead body channels is associated with a different one of the two exit openings and a different one of the two slits, wherein each of the two lead body channels is configured and arranged to receive a one of the at least one lead body extending from the paddle body of the paddle lead;

a stylet channel extending along the longitudinal length of the insertion tool body from the receiving end portion to the handling end portion and open to the two lead body channels;

a stylet disposed in the stylet channel and comprising a stylet head disposed in the receiving end portion of the insertion tool body, the stylet configured and arranged for transitioning between a first position and a second position, wherein when the stylet transitions from the first to the second position, the stylet head pushes any lead body in the two lead body channels of the insertion tool body out of the insertion tool through a one of the two slits to release the lead body from the insertion tool; and an actuator assembly disposed along the handling end portion of the insertion tool body and coupled to the stylet, the actuator assembly configured and arranged to control transitioning of the stylet between the first position and the second position.

2. The insertion tool of claim 1, wherein the first position is a retracted position and the second position is an extended position.

3. The insertion tool of claim 2, wherein the stylet head is tapered with a narrower portion of the stylet head nearer the distal end of the receiving end portion than a wider portion of the stylet head.

4. The insertion tool of claim 1, wherein the first position is an extended position and the second position is a retracted position.

5. The insertion tool of claim 4, wherein the stylet head is tapered with a narrower portion of the stylet head further from the distal end of the receiving end portion than a wider portion of the stylet head.

6. The insertion tool of claim 1, wherein the actuator assembly comprises an actuator handle configured to slide to transition the stylet from the first position to the second position.

7. The insertion tool of claim 1, wherein the actuator assembly comprises an actuator button and a stylet holding mechanism coupled to the actuator button and the stylet.

8. The insertion tool of claim 1, wherein the stylet head is wider than a separation distance between the two lead body channels.

9. The insertion tool of claim 1, wherein the insertion tool body comprises at least one curve.

10. The insertion tool of claim 9, wherein the insertion tool body comprises a first curve positioned along the receiving end portion and a second curve positioned along the handling end portion.

11. The insertion tool of claim 10, wherein the first and second curves are oriented to form an S-shaped configuration along the longitudinal length of the insertion tool body.

12. The insertion tool of claim 1, wherein the stylet head has an arrow-like shape.

13. A system for implanting a paddle lead, the system comprising:
the insertion tool of claim 1, and
the paddle lead comprising a paddle body, at least one lead body extending from the paddle body, and a plurality of electrodes disposed on the paddle body.

14. The system of claim 13, wherein the at least one lead body of the paddle lead is two lead bodies.

15. A method of implanting a paddle lead, the method comprising:
inserting a distal portion of at least one lead body of the paddle lead into at least one of the lead body channels of the insertion tool of claim 1, the at least one lead body coupled to a paddle body of the paddle lead;
inserting the paddle body of the paddle lead into patient tissue; and
operating the actuator assembly of the insertion tool to move the stylet and push the distal portion of the at least one lead body of the paddle lead out of at least one of the two slits of the insertion tool.

16. The method of claim 15, wherein the paddle lead comprises two lead bodies and the inserting step comprises inserting the distal portion of each of the two lead bodies of the paddle lead into different ones of the lead body channels of the insertion tool.

17. The method of claim 15, wherein the inserting step comprises inserting the distal portion of the at least one lead body of the paddle lead into the at least one of the lead body channels of the insertion tool, wherein a remainder of the at least one lead body exits through at least one of the exit openings and is disposed outside of the insertion tool.

18. The method of claim 15, wherein operating the actuator assembly comprises operating the actuator assembly to push the stylet forward.

19. The method of claim 15, wherein operating the actuator assembly comprises operating the actuator assembly to pull the stylet backward.

20. The method of claim 15, further comprising, after pushing the at least one lead body of the paddle lead out of the at least one of the two slits of the insertion tool, withdrawing the insertion tool.

* * * * *